United States Patent
Gidner et al.

(10) Patent No.: US 9,408,852 B2
(45) Date of Patent: Aug. 9, 2016

(54) METHOD OF LOWERING SERUM URIC ACID LEVELS WITH (S)-TOFISOPAM

(75) Inventors: Judi Gidner, Yardley, PA (US); Karen Raudibaugh, North Wales, PA (US); Brian Speicher, Hackensack, NJ (US)

(73) Assignee: PHARMOS CORPORATION, West Palm Beach, FL (US)

( * ) Notice: Subject to any disclaimer, the term of this patent is extended or adjusted under 35 U.S.C. 154(b) by 849 days.

(21) Appl. No.: 13/558,491

(22) Filed: Jul. 26, 2012

(65) Prior Publication Data

US 2013/0045966 A1 Feb. 21, 2013

Related U.S. Application Data

(60) Provisional application No. 61/512,114, filed on Jul. 27, 2011.

(51) Int. Cl.
*A61K 31/551* (2006.01)
*A61P 9/12* (2006.01)
*A61P 13/12* (2006.01)
*A61P 19/06* (2006.01)
*A61K 45/06* (2006.01)

(52) U.S. Cl.
CPC ............... *A61K 31/551* (2013.01); *A61K 45/06* (2013.01)

(58) Field of Classification Search
None
See application file for complete search history.

(56) References Cited

U.S. PATENT DOCUMENTS

| 6,649,607 B2 | 11/2003 | Leventer et al. |
| 6,864,251 B2 | 3/2005 | Kucharik et al. |
| 7,078,398 B2 | 7/2006 | Leventer et al. |
| 2004/0138209 A1 | 7/2004 | Kucharik et al. |
| 2004/0162284 A1 | 8/2004 | Harris et al. |
| 2004/0229866 A1 | 11/2004 | Harris et al. |
| 2005/0288277 A1* | 12/2005 | Kucharik et al. ............. 514/221 |
| 2007/0032479 A1 | 2/2007 | Leventer et al. |

OTHER PUBLICATIONS

Kelley, A Specific Enzyme Defect in Gout Associated with Overproduction of Uric Acid, Biochemistry, 1967, 57, pp. 1735-1739.*
Aug. 2010, Pharmos Presentation, S. Colin Neill, pp. 1-21.
Form 10-Q from Pharmos 3rd quarter, filed Oct. 27, 2010, pp. 1-31 and Exhibit 31.1, 31.2, 32.1 and 32.2.
Feb. 17, 2011 Pharmos Press Release, pp. 1-4.

* cited by examiner

*Primary Examiner* — San-Ming Hui
*Assistant Examiner* — Andrew Lee
(74) *Attorney, Agent, or Firm* — Drinker Biddle & Reath LLP

(57) ABSTRACT

Enantiomerically-pure (S)-tofisopam is administered to lower serum uric acid levels in a mammal.

19 Claims, No Drawings

METHOD OF LOWERING SERUM URIC ACID LEVELS WITH (S)-TOFISOPAM

CROSS-REFERENCE TO RELATED APPLICATIONS

This application claims the benefit of U.S. Provisional Application No. 61/512,114, filed Jul. 27, 2011, the entire disclosure of which is incorporated herein by reference.

FIELD OF THE INVENTION

The present invention relates to methods of lowering serum uric acid levels in a mammal.

BACKGROUND OF THE INVENTION 2,3-Benzodiazenines—Tofisopam

Tofisopam (1-(3,4-dimethoxyphenyl)-4-methyl-5-ethyl-7,8-dimethoxy-5H-2,3-benzodiazepine) is an exemplary 2,3-benzodiazepine molecule. Tofisopam is a non-sedative anxiolytic that has no appreciable sedative, muscle relaxant or anticonvulsant properties (Horvath et al., *Progress in Neurobiology*, 60 (2000), 309-342).

Tofisopam is a racemic mixture of (R)- and (S)-enantiomers. The chiral nature of tofisopam is due to the asymmetric carbon, at the 5-position of the benzodiazepine ring, attached with four different groups. Differential therapeutic effects have been noted for either cnantiomer. For example, the (R)-enantiomer of tofisopam has been isolated and shown to possess the nonsedative anxiolytic activity of the racemic mixture. See U.S. Pat. No. 6,080,736, the entire disclosure of which is incorporated herein by reference. Furthermore, the (R)-enantiomer has been shown to have a differential effect in the treatment of leukotriene B4-mediated disease. See U.S. Pat. No. 6,864,251, the entire disclosure of which is incorporated by reference. The (S)-enantiomer has been isolated and shown to possess an anticonvulsant activity. See U.S. Pat. No. 6,649,607; the entire disclosure of which is incorporated herein by reference. Similarly, the (S)-enantiomer has been shown to be effective in lowering body temperature, as in minimizing hot flashes. See US Patent Publication 2004/0229866, the entire disclosure of which is incorporated herein by reference.

Hyperuricemia

Hyperuricemia is a disease characterized by an abnormally high level of uric acid in the plasma. When the concentration of uric acid in the blood exceeds a certain level, uric acid precipitates as monosodium urate and may deposit in various tissues, such as the cavitas articulare or kidney. Hyperuricemia may be caused by reduced excretion of uric acid, by its excessive production, or by a combination of both. It may also result from other diseases, such as an enzymatic abnormality in purine metabolism. These are all so-called "primary cause" diseases. Examples of these "primary cause" diseases include gout (including acute gouty arthritis and chronic tophaceous arthritis), urinary calculus, hyperuricemic nephropathy (chronic gouty nephropathy, acute hyperuricemic nephropathy) and Lesch-Nyhan syndrome. Other diseases, such as disorders of the hemocytopoictic organs and renal disorders, and disorders resulting from the administration of a medicament, such as pyrazinamide or thiazide, may also result in hyperuricemia, and are typically referred to as "secondary cause" diseases. (See U.S. Pat. No. 6,353,009, herein incorporated by reference).

Gout is characterized by a disturbance of uric-acid metabolism occurring chiefly in males. Gout is characterized by painful inflammation of the joints, especially of the feet and hands, and arthritic attacks resulting from elevated levels of uric acid in the blood serum and the deposition of urate crystals around the joints. The condition can become chronic and result in deformity.

Gout can present another circumstance wherein it is known beforehand that an individual will or is likely to develop an inflammatory disorder. In the instance of patients undergoing radiotherapy or chemotherapy, the individual may experience a dramatic rise in serum uric acid levels associated with lysis of the tumor mass. Such large increases in uric acid can deposit urate crystals in synovial fluid of joints thereby causing the inflammatory disorder, gout. When such a rise in uric acid levels is known to be likely, prophylaxis with (S)-tofisopam can act to prevent the inflammatory condition of gout.

A number of treatments exist for hyperuricemia. However, none of these treatments have been totally efficacious in the treatment of hyperuricemia. The present invention provides a novel, effective method for the treatment of hyperuricemia.

SUMMARY OF THE INVENTION

According to one embodiment of the invention there is provided a method of lowering serum uric acid levels of a mammal, comprising administering to the mammal an effective amount of enantiomerically-pure (S)-tofisopam, or a pharmaceutically acceptable salt thereof. In preferred embodiments, the enantiomerically-pure (S)-tofisopam is administered with a second drug. In some preferred embodiments the second drug is a drug for treating hypertension. In some preferred embodiments the enantiomerically-pure (S)-tofisopam comprises 85% by weight or greater of (S)-tofisopam. In some preferred embodiments the enantiomerically-pure (S)-tofisopam comprises 90% by weight or greater of (S)-tofisopam. In further preferred embodiments the enantiomerically-pure (S)-tofisopam comprises 95% by weight or greater of (S)-tofisopam. In yet further preferred embodiments the enantiomerically-pure (S)-tofisopam comprises 99% by weight or greater of (S)-tofisopam. In some embodiments, the uric acid is excreted.

In some preferred embodiments, the mammal is afflicted with a disorder associated with elevated uric acid levels. In further preferred embodiments, the disorder is selected from the group consisting of gout, urinary calculus, hyperuricemic nephropathy, Lesch-Nyhan syndrome, disorders of the hemocytopoietic organs, renal disorders, hypertension and disorders resulting from the administration of a medicament. In especially preferred embodiments, the disorder is gout. In further especially preferred embodiments, the disorder is Lesch-Nyhan syndrome.

According to some preferred embodiments, enantiomerically-pure (S)-tofisopam, or a pharmaceutically acceptable salt thereof, is administered at a daily dosage of 10 to 1500 mg/day. In some preferred embodiments, enantiomerically-pure (S)-tofisopam, or a pharmaceutically acceptable salt thereof, is administered at a daily dosage of 25 to 500 mg/day. In further preferred embodiments, the enantiomerically-pure (S)-tofisopam, or a pharmaceutically acceptable salt thereof, is administered at a daily dosage of 50 to 400 mg/day. According to further preferred embodiments, the daily dosage of enantiomerically-pure (S)-tofisopam, or a pharmaceutically acceptable salt thereof, is administered as a single daily dose. In some preferred embodiments, the daily dosage of enantiomerically-pure (S)-tofisopam, or a pharmaceutically acceptable salt thereof, is split into two, three or more doses per day.

According to some preferred embodiments, the enantiomerically-pure (S)-tofisopam, or a pharmaceutically acceptable salt thereof, is administered orally.

According to some preferred embodiments, the enantiomerically-pure (S)-tofisopam, or a pharmaceutically acceptable salt thereof, is administered at a dosage of 50 mg, three times a day.

According to further preferred embodiments, the enantiomerically-pure (S)-tofisopam, or a pharmaceutically acceptable salt thereof, is administered as a single daily dose of 50 mg, 100 mg, 200 mg, 300 mg or 400 mg.

In some embodiments, the level of serum creatinine in the mammal is not substantially affected when the mammal is treated with enantiomerically-pure (S)-tofisopam, or a pharmaceutically acceptable salt thereof.

Definitions

The phrase "optically active" refers to a property whereby a material rotates the plane of plane-polarized light. A compound that is optically active is nonsuperimposable on its mirror image. The property of nonsuperimposablity of an object on its mirror image is called chirality.

The property of "chirality" in a molecule may arise from any structural feature that makes the molecule nonsuperimposable on its mirror image. The most common structural feature producing chirality is an asymmetric carbon atom, i.e., a carbon atom having four nonequivalent groups attached thereto.

The term "effective amount" when used to describe therapy to a patient to lower uric acid, refers to the amount of enantiomerically-pure (S)-tofisopam that results in a therapeutically useful reduction in serum uric acid levels when administered to a patient suffering from a disorder which manifests elevated serum uric acid levels. Further, the term "effective amount" may be used to refer to the amount of a compound of enantiomerically-pure (S)-tofisopam that results in a therapeutically useful reduction in serum uric acid levels when administered to a patient suffering from disorder which is effectively treated by lowering serum uric acid levels.

The term "enantiomer" refers to each of the two nonsuperimposable isomers of a pure compound that is optically active. Single enantiomers are designated according to the Cahn-Ingold-Prelog system, a set of priority rules that rank the four groups attached to an asymmetric carbon. See March, Advanced Organic Chemistry, 4$^{th}$ Ed., (1992), p. 109. Once the priority ranking of the four groups is determined, the molecule is oriented so that the lowest ranking group is pointed away from the viewer. Then, if the descending rank order of the other groups proceeds clockwise, the molecule is designated R and if the descending rank of the other groups proceeds counterclockwise, the molecule is designated S. In the example below, Cahn-Ingold-Prelog ranking sequence is A>B>C>D. The lowest ranking atom, D, is oriented away from the viewer.

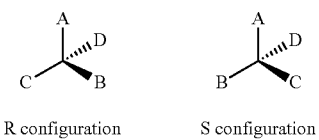

R configuration    S configuration

The term "racemate" or the phrase "racemic mixture" refers to a 50-50 mixture of the (R)- and (S)-enantiomers of a compound such that the mixture does not rotate plane-polarized light.

The term "enantiomerically-pure" when used to refer to a compound, means the (R)- or (S)-enantiomers of the compound have been separated such that the composition is 80% or more by weight a single enantiomer. Thus, by "enantiomerically-pure (S)-tofisopam" is meant tofisopam that comprises 80% or more by weight of the (S)-enantiomer and likewise contains 20% or less of the (R)-enantiomer as a contaminant, by weight.

The term "disorder associated with elevated uric acid levels" refers to a disorder that is associated with a reduced excretion of uric acid, with its excessive production or with a combination of both. A "disorder associated with elevated uric acid levels" may also result from other diseases, such as an enzymatic abnormality in the purine metabolism. These are all so-called "primary cause" diseases. Examples of these "primary cause" diseases include gout (including acute gouty arthritis and chronic tophaceous arthritis), urinary calculus, hyperuricemic nephropathy (chronic gouty nephropathy, acute hyperuricemic nephropathy) and Lesch-Nyhan syndrome. A "disorder associated with elevated uric acid levels" may also result from other diseases, such as disorders of the hemocytopoictic organs and renal disorders, and disorders resulting from the administration of a medicament, such as pyrazinamide or thiazide. Such disorders may also result in hyperuricemia, and are typically referred to as "secondary cause" diseases. (See U.S. Pat. No. 6,353,009, herein incorporated by reference).

The term "mammal", "individual" or "subject", includes human beings and non-human animals.

DETAILED DESCRIPTION OF THE INVENTION

According to the present invention, (S)-tofisopam, or pharmaceutically acceptable salts thereof, is useful in methods for lowering serum uric acid levels in a mammal. (S)-tofisopam has demonstrated therapeutic activity in the reduction of serum uric acid levels in a subject.

According to one embodiment of the invention, there is provided a method of lowering serum uric acid levels of an individual afflicted with a disorder associated with elevated uric acid levels, said method comprising administering to the subject an effective amount of (S)-tofisopam.

Such disorders include, but are not limited to, gout (including acute gouty arthritis and chronic tophaceous arthritis), urinary calculus, hyperuricemic nephropathy (chronic gouty nephropathy, acute hyperuricemic nephropathy), Lesch-Nyhan syndrome, disorders of the hemocytopoietic organs and renal disorders, hypertension and disorders resulting from the administration of a medicament, such as pyrazinamide or thiazide.

Preparation of (S)-Tofisopam (S)-tofisopam may be prepared by one of several methods. These methods generally begin with synthetic strategies and procedures used in the synthesis of racemic 2,3-benzodiazepines, e.g., for example, tofisopam, and further include a resolution of the racemate to isolate the (S)-enantiomers or (R)-enantiomers. See U.S. Pat. Nos. 3,736,315 and 4,423,044 (tofisopam syntheses) and Horvath et al., *Progress in Neurobiology* 60 (2000) p. 309-342 and references cited therein (preparation of tofisopam and analogs thereof), the entire disclosures of which are incorporated herein by reference.

In the synthesis methods that follow, the product of the chemical syntheses is a racemic tofisopam. This racemic mixture is subsequently separated using known methods of resolution to produce (S)-tofisopam, substantially free of (R)-tofisopam, i.e., to produce enantiomerically-pure (S)-tofisopam. Preferably, the compound used in methods of the present invention has a composition that is 85% by weight or greater of (S)-tofisopam, and 15% by weight, or less, of (R)-tofisopam. More preferably, the compound used in methods of the present invention has a composition that is 90% by weight or greater of (S)-tofisopam and 10% by weight, or less, of (R)-tofisopam. More preferably, the compound used in the methods of the present invention has a composition that is 95% by weight or greater of (S)-tofisopam and 5% by weight; or less, of (R)-tofisopam. Most preferably, the compound used in methods of the present invention has a composition that is 99% by weight or greater of (S)-tofisopam and 1% by weight, or less, of (R)-tofisopam.

Racemic mixtures containing (S)-tofisopam may be synthesized, as shown in Scheme 1, which exemplifies the preparation of racemic tofisopam. The racemic 2,3-benzodiazepine is prepared from the corresponding 2-benzopyrilium salt H by reaction with hydrazine hydrate, wherein X⁻ is a counterion such as, for example perchlorate:

Scheme 1

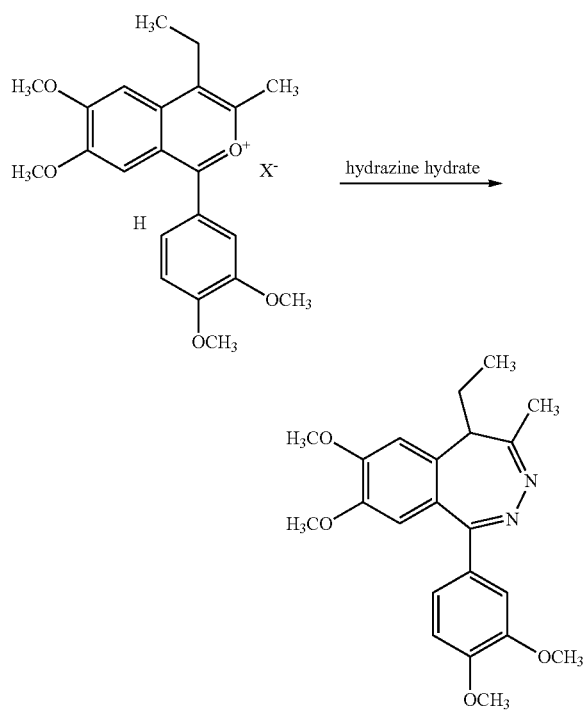

According to Scheme 1, hydrazine hydrate (98%, approximately 3 equivalents based on the 2-benzopyrylium salt) is added dropwise to a stirred solution of the 2-benzopyrylium salt H in glacial acetic acid (approximately 1 mL/3 mmol of 2-benzopyrylium salt). During this operation, the solution is maintained at an elevated temperature, preferably, 80-100° C. The solution is then maintained at an elevated temperature, preferably 95-100° C. for about one hour. Then the reaction mixture is diluted with 2% aqueous sodium hydroxide solution (approximately 3 equivalents based on the 2-benzopyrylium salt) and cooled. The product 2,3-benzodiazepine separates as a solid and is removed by filtration, washed with water and dried. The crude product may be purified by taking it up in a polar aprotic solvent such as dimethylformamide (DMF) at an elevated temperature, preferably 100-130° C. and decolorizing the solution with activated carbon. The carbon is removed by filtration and the filtered solution is diluted with water. The purified product precipitates out of the solution and is collected by filtration. See Kórósi et al., U.S. Pat. No. 4,322,346, the entire disclosure of which is incorporated herein by reference, disclosing three variations of the reaction protocol for preparing a substituted 2,3-benzodiazepine from the precursor benzopyrilium salt.

Retrosynthetically, the intermediate benzopyrilium salt, H, may be prepared from one of several starting materials. According to one such method, illustrated in Scheme 2, intermediate H is prepared from the corresponding aryl ethanol derivative D (3-(3,4-dimethoxyphenyl)pentan-2-ol) via the isochroman intermediate F (1-(3,4-dimethoxyphenyl)-4-ethyl-6,7-dimethoxy-3-methylisochromane) wherein X⁻ is a counterion such as, for example perchlorate.

Scheme 2

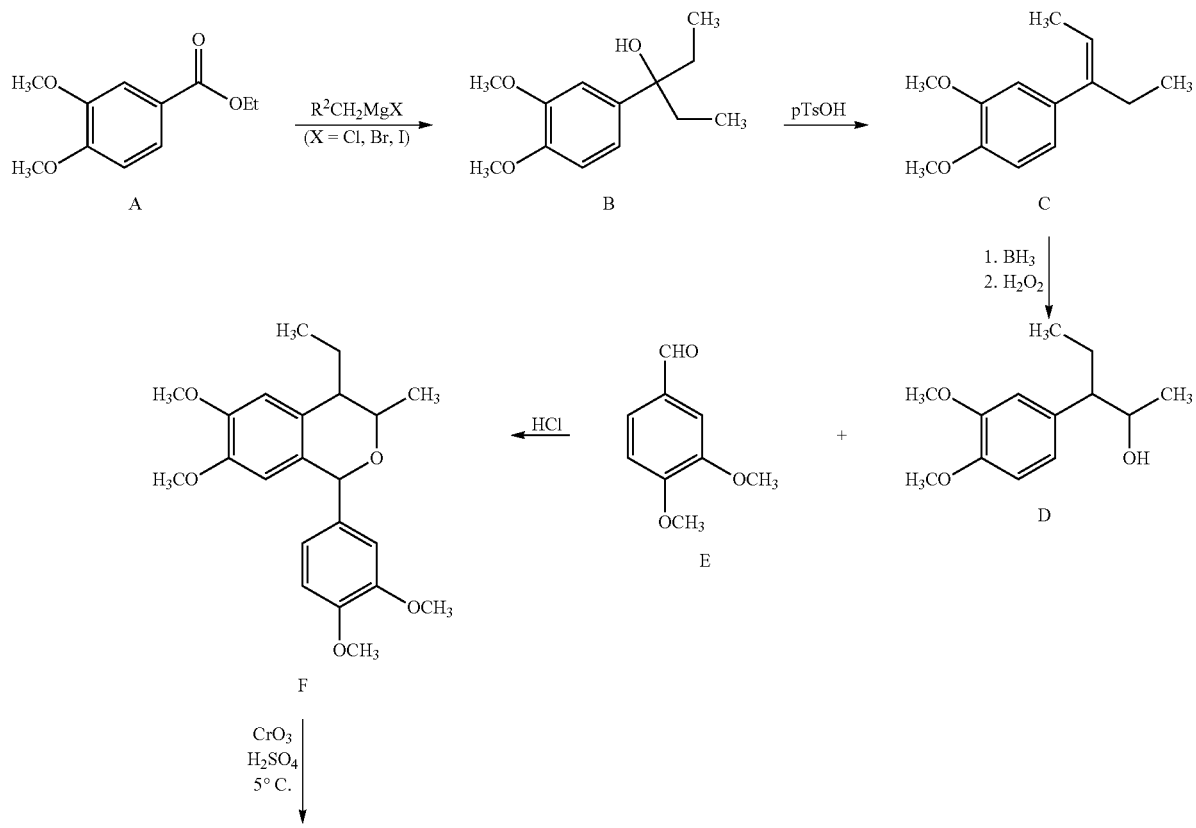

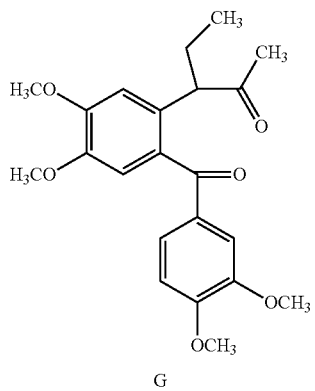

G

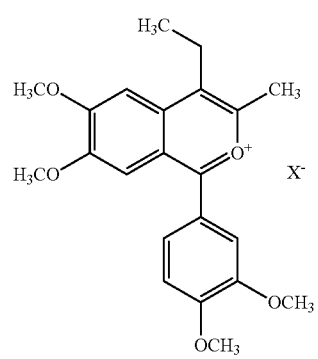

H

According to Scheme 2, ethyl-3,4-dimethoxybenzoate, A is dissolved in a suitable solvent, preferably ether and cooled to 0° C. Two equivalents of an ethyl Grignard reagent, such as ethyl magnesium iodide is added dropwise and the reaction is allowed to warm to room temperature and monitored for disappearance of starting material. When the reaction is complete, it may be quenched with a proton source such as acetic acid. Volatiles are removed in vacuo, and the product B (3-(3,4-dimethoxyphenylpentan-3-ol) is used for the next step without purification.

3-(3,4-Dimethoxyphenyl)pentan-3-ol, B, is taken up in a high boiling solvent such as toluene and a catalytic amount of para-toluene sulfonic acid (p-TsOH). The mixture is warmed to reflux and may be monitored for disappearance of starting materials. When the reaction is complete, the volatiles are removed in vacuo and the crude product C (4-((1Z)-1-ethyl-prop-1-enyl)-1,2-dimethoxybenzene) is purified by column chromatography.

4-((1Z)-1-Ethylprop-1-enyl)-1,2-dimethoxybenzene, C is hydroxylated under anti-Markovnikov conditions to give intermediate D (3-(3,4-dimethoxyphenyl)pentan-2-ol). A solution of D, and of 3,4-dimethoxybenzaldehyde, E (1.2 eq) are dissolved in anhydrous dioxane. The resulting solution is then saturated with gaseous HCl and warmed, preferably to reflux temperature for about one hour. The mixture is then cooled to room temperature, poured into water, basified, preferably with aqueous sodium hydroxide and extracted with an organic solvent, preferably ethyl acetate. The extract is dried, filtered and concentrated under vacuum. The resulting residue is purified, preferably by crystallization to yield F (1-(3,4-dimethoxyphenyl)-4-ethyl-6,7-dimethoxy-3-methylisochromane).

To a stirred, cooled, (preferably to 0-5° C.) solution of F (2 g) in acetone (30 mL), is added dropwise a solution of chromium trioxide (2 g) in 35% sulfuric acid (20 mL); added at a rate such that the reaction temperature remains below 5° C. After the addition is complete, the reaction mixture is allowed to rise to room temperature and is stirred at room temperature for two hours. The reaction mixture is then poured into water and extracted with an organic solvent, preferably ethyl acetate. The organic extract is washed with water and then with ice-cold 10% aqueous sodium hydroxide. The aqueous alkaline fraction is then acidified, preferably with dilute aqueous hydrochloric acid and extracted with an organic solvent, preferably, chloroform. The chloroform extract is dried, filtered and concentrated under vacuum to give G (3-{2-[(3,4-dimethoxyphenyl)carbonyl]-4,5-dimethoxyphenyl}pentan-2-one). The crude residue may further be purified by column chromatography.

G (5 g) is dissolved in glacial acetic acid (15 mL). To this mixture was added 60% perchloric acid (7.5 mL). The resulting mixture is warmed to 100° C. (steam bath) for three minutes. The mixture is allowed to cool to room temperature. Crystallization of the crude product may begin spontaneously at this point or may be induced by addition to the reaction mixture of ether or ethyl acetate. The product 2-benzopyrylium salt H is removed by filtration and purified by recrystallization, preferably from ethanol or glacial acetic acid/ethyl acetate.

A similar synthetic sequence for preparation of 2,3-benzodiazepines is disclosed in U.S. Pat. No. 3,736,315, the entire disclosure of which is incorporated herein by reference. Synthetic strategies for preparation of 2,3-benzodiazepines are disclosed in Horvath et al., *Progress in Neurobiology* 60 (2000) p. 309-342 and references cited therein; the entire disclosures of which are incorporated herein by reference. These synthetic sequences may be used to prepare racemic tofisopam.

Alternative methods for preparation of intermediate H start with an aryl acetonide or indanone starting material. See Kunnetsov, E. V., and Dorofeenko, G. N., *Zh. Org. Khim.*, 6, 578-581 and M. Vajda, *Acta Chem. Acad. Sci. Hung.*, 40, p. 295-307, 1964, respectively.

Resolution of Racemic Tofisopam

The synthetic procedures shown (or referenced) above produce racemic tofisopam which may be employed in this invention. In order to provide the (S)-tofisopam useful in methods of the present invention, the racemic mixture must be resolved.

A racemic tofisopam may be converted to the (S)-dibenzoyltartaric acid salt, which is a diastereomeric mixture of SS and RS configurations. The pair of diastereomers (R,S) and (S,S) possess different properties, e.g., differential solubilities, that allow for the use of conventional separation methods. Fractional crystallization of diastereomeric salts from a suitable solvent is one such separation method. This resolution has been successfully applied to the resolution of racemic toifsopam. See Hungarian Patent 178516 and also Toth et al., *J. Heterocyclic Chem.*, 20:09-713 (1983), the entire disclosures of which are incorporated herein by reference.

Racemic tofisopam may also be resolved without diastereomer formation by differential absorption on a chiral stationary phase of a chromatography column, particularly a preparative HPLC column. Chiral HPLC columns are commercially available with a variety of packing materials to suit a broad range of separation applications. Exemplary stationary phases suitable for resolving the racemic tofisopam include:

(i) macrocyclic glycopeptides, such as silica-bonded vancomycin which contains 18 chiral centers surrounding three pockets or cavities;

(ii) chiral α₁-acid glycoprotein;

(iii) human serum albumin; and (iv) cellobiohydrolase (CBH).

Chiral α₁-acid glycoprotein is a highly stable protein immobilized onto spherical silica particles that tolerates high concentrations of organic solvents, high and low pH, and high temperatures. Human serum albumin, though especially suited for the resolution of weak and strong acids, zwitterionic and nonprotolytic compounds, has been used to resolve basic compounds. CBH is a very stable enzyme that has been immobilized onto spherical silica particles and is preferentially used for the separation of enantiomers of basic drugs from many compound classes.

The resolution of tofisopam by chiral chromatography using macrocyclic glycopeptide as a stationary phase on a Chirobiotic V™ column (ASTEAC, Whippany, N.J.) is disclosed in U.S. Pat. No. 6,080,736. Fitos et al. (*J. Chromatogr.*, 709 265 (1995)), discloses another method for resolving racemic tofisopam by chiral chromatography using a chiral ∩₁-acid glycoprotein as a stationary phase on a CHIRAL-AGP™ column (ChromTech, Cheshire, UK). This method separates the (R)- and (S)-enantiomers and also resolves the two conformers (discussed below) of each enantiomer. The Chirobiotic V™ column is available in a semi-preparative size as employed for the above separation (500 mm×10 mm). In addition, the stationary phase of the Chirobiotic V™ column is commercially available in bulk for packing of preparative chromatography columns with larger sample capacity. The entire disclosures of the aforementioned patents and publications are incorporated herein by reference in their entireties. The disclosed methods may be utilized for resolving not only tofisopam, but also any other racemic 2,3-benzodiazepines.

In addition to existing as (R)- and (S)-enantiomers, tofisopam may also exist in two stable conformations that may be assumed by the benzodiazepine ring as generally depicted below.

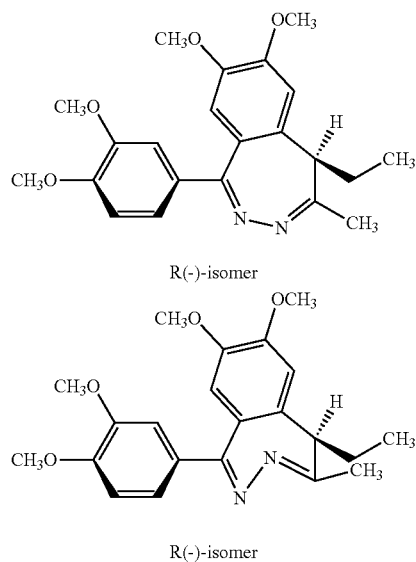

R(-)-isomer

R(-)-isomer

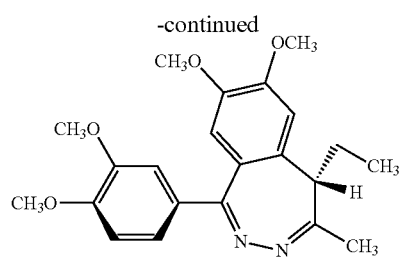

S(-)-isomer

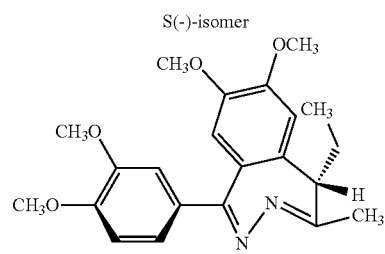

S(-)-isomer

The present invention includes methods as described herein that use any and all observable conformations of enantiomerically-pure (S)-tofisopam.

Enantiomerically-pure (S)-tofisopam used in the practice of methods of the present invention may take the form of pharmaceutically-acceptable salts. The term "salts", embraces salts commonly used to form alkali metal salts and to form addition salts of free acids or free bases. The term "pharmaceutically-acceptable salt" refers to salts that possess toxicity profiles within a range so as to have utility in pharmaceutical applications. Pharmaceutically unacceptable salts may nonetheless possess properties such as high crystallinity, which have utility in the practice of the present invention, such as for example utility in a synthetic process or in the process of resolving enantiomers from a racemic mixture.

Suitable pharmaceutically-acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, 4-hydroxybenzoic, phenylacetic, mandelic, embonic (pamoic), methanesulfonic, pantothenic, ethanesulfonic, benzenesulfonic, 2-hydroxyethanesulfonic, toluenesulfonic, sulfanilic, cyclohexylaminosulfonic, stearic, algenic, beta-hydroxybutyric, galactaric and galacturonic acid.

Administration of Enantiomerically-Pure (S)-Tofisopam

The enantiomerically-pure (S)-tofisopam may be administered to individuals (mammals, including animals and humans) afflicted with disorders associated with elevated uric acid or with disorders wherein lowering the level of uric acid below the normal level of uric acid has therapeutic benefit. For treating or preventing disorders associated with elevated uric acid or disorders wherein lowering the level of uric acid below the normal level of uric acid has therapeutic benefit, the specific dose of enantiomerically-pure (S)-tofisopam to obtain therapeutic benefit will, of course, be determined by the particular circumstances of the individual patient including, the size, weight; age and sex of the patient. Also determinative will be the nature and stage of the disease and the route of administration. For example, a daily dosage of from about 10 to 1500 mg/day may be utilized. Preferably, a daily dosage of from about 25 to 500 mg/day may be utilized. More preferably, a daily dosage of from about 50 to 400 mg/day may be utilized. Higher or lower doses are also contemplated. The daily dosage of enantiomerically-pure (S)-tofisopam may be given in one dose per day or may be split into two, three or more doses per day.

For prophylactic administration, enantiomerically-pure (S)-tofisopam should be administered far enough in advance of a known event that increases uric acid levels, such that the compound is able to reach the site of action in sufficient concentration to exert the desired effect. The pharmacokinetics of specific formulations may be determined by means known in the art and tissue levels of enantiomerically-pure (S)-tofisopam in a particular individual may be determined by conventional analyses.

The methods of the present invention may comprise administering enantiomerically-pure (S)-tofisopam in the form of a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient that is compatible with the other ingredients of the formulation and not deleterious to the recipient.

Where the enantiomerically-pure (S)-tofisopam and the one or more additional therapeutic agents are administered at different times, the administration times are preferably optimized to obtain the therapeutic effect on serum uric acid levels by the combination, based on the pharmacokinetic profiles of the compounds administered.

The enantiomerically-pure (S)-tofisopam and the second drug may be administered simultaneously, by the same or different routes, or at different times during treatment or prevention therapy.

Where the enantiomerically-pure (S)-tofisopam and the second drug are administered simultaneously, the administration may be by the same or by different routes. Preferably, simultaneous administration is done by administering the compounds as part of the same pharmaceutical composition.

In preferred embodiments, the enantiomerically-pure (S)-tofisopam is administered with a second drug. In some preferred embodiments the second drug is a drug for treating hypertension. A person of skill in the art would know at what times and with what dosage and frequency to administer the second drug in order to obtain the desired improvement of the hypertension of the patient.

The enantiomerically-pure (S)-tofisopam may be administered for therapeutic effect by any route, for example enteral (e.g., oral, rectal, intranasal, etc.) and parenteral administration. Parenteral administration includes, for example, intravenous, intramuscular, intraarterial, intraperitoneal, intravaginal, intravesical (e.g., into the bladder), intradermal, topical or subcutaneous administration. Also contemplated within the scope of the invention is the instillation of drug in the body of the patient in a controlled formulation, with systemic or local release of the drug to occur at a later time.

The enantiomerically-pure (S)-tofisopam is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences,* 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the enantiomerically-pure (S)-tofisopam may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water-soluble salt of the active agent. Stabilizing agents, antioxidizing agents and preservatives may also be added. Suitable antioxidizing agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or nonaqueous solution, dispersion, suspension or emulsion.

For oral administration, the enantiomerically-pure (S)-tofisopam may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The compositions of the present invention can also be formulated so as to provide slow or controlled-release of the active ingredient therein. In general, a controlled-release preparation is a composition capable of releasing the active ingredient at the required rate to maintain constant pharmacological activity for a desirable period of time. Such dosage forms can provide a supply of a drug to the body during a predetermined period of time and thus maintain drug levels in the therapeutic range for longer periods of time than other non-controlled formulations.

For example, U.S. Pat. No. 5,674,533 discloses controlled-release compositions in liquid dosage forms for the administration of moguisteine, a potent peripheral antitussive. U.S. Pat. No. 5,059,595 describes the controlled-release of active agents by the use of a gastro-resistant tablet for the therapy of organic mental disturbances. U.S. Pat. No. 5,591,767 discloses a liquid reservoir transdermal patch for the controlled administration of ketorolac, a non-steroidal anti-inflammatory agent with potent analgesic properties. U.S. Pat. No. 5,120,548 discloses a controlled-release drug delivery device comprised of swellable polymers. U.S. Pat. No. 5,073,543 discloses controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. The patents cited above are incorporated herein by reference.

Biodegradable microparticles can be used in the controlled-release formulations of this invention. For example, U.S. Pat. No. 5,354,566 discloses a controlled-release powder that contains the active ingredient. U.S. Pat. No. 5,733,566 describes the use of polymeric microparticles that release antiparasitic compositions. These patents are incorporated herein by reference.

The controlled-release of the active ingredient may be stimulated by various inducers, for example pH, temperature, enzymes, water, or other physiological conditions or compounds. Various mechanisms of drug release exist. For example, in one embodiment, the controlled-release component can swell and form porous openings large enough to release the active ingredient after administration to a patient. The term "controlled-release component" in the context of the present invention is defined herein as a compound or compounds, such as polymers, polymer matrices, gels, permeable membranes, liposomes and/or microspheres, that facilitate the controlled-release of the active ingredient in the pharmaceutical composition. In another embodiment, the controlled-release component is biodegradable, induced by exposure to the aqueous environment, pH, temperature, or enzymes in the body. In another embodiment, sol-gels can be used, wherein the active ingredient is incorporated into a sol-gel matrix that is a solid at room temperature. This matrix is implanted into a patient, preferably a mammal, having a body temperature high enough to induce gel formation of the sol-gel matrix, thereby releasing the active ingredient into the patient.

Enantiomerically-pure (S)-tofisopam is administered according to the present invention to patients suffering from conditions that manifest the symptom of hyperuricemia. Such conditions include for example, serotonin syndrome and malignant hyperthermia. In addition, the active agent is administered according to the present invention to patients suffering from conditions that are associated with hyperuricemia. Such conditions include for example, gout.

The practice of the invention is illustrated by the following non-limiting examples.

EXAMPLES

Example 1

Preparation of Enantiomerically-Pure (S)-Tofisopam

A. Synthesis of Racemic Tofisopam:

4.41 g (10 mmol) of 1-(3,4-dimethoxyphenyl)-3-methyl-4-ethyl-6,7-dimethoxyisobenzopyrilium chloride hydrochloride is dissolved in methanol (35 mL) at a temperature of 40° C. After cooling to 20-25° C., hydrazine hydrate (0.75 g, 15 mmol, dissolved in 5 mL methanol) is added. The reaction is monitored by HPLC and when complete, is evaporated to dryness. The residue is triturated with cold water (3 mL), filtered and dried to yield the crude (R,S)-1-(3,4-dimethoxyphenyl)-4-methyl-5-ethyl-7-hydroxy-8-methoxy-5H-2,3-benzodiazepine which is subsequently triturated with hot ethyl acetate to yield the pure product.

B. Resolution of Racemic Tofisopam to Produce Enantiomerically-Pure (S)-Tofisopam:

The enantiomers of tofisopam are resolved by chiral chromatography. For example, tofisopam (42.8 mg dissolved in acetonitrile (ACN)) is loaded onto a Chirobiotic V column (ASTEC, Whippany, N.J.). Elution of the compounds with methyl-tert-butyl ether (MTBE)/ACN 90/10 (v/v), 40 mL/min, is monitored at 310 nm, 2 mm path. The R(+) enantiomer is the first compound to elute from the column. R(−) tofisopam ("peak A'"), S(−/+) tofisopam ("peak B" and "peak B'"), and residual R(+) tofisopam ("A") coelute and are collected in a subsequent fraction.

The S(−) enantiomer may be isolated from the subsequent fraction by the following protocol. The subsequent fraction is dried, redissolved in 1 mL of ACN and loaded onto a Chirobiotic V column. Peak B and B' is shave recycled over a Chirobiotic V column two more times (MTBE/ACN 90/10 (v/v), 40 mL/min monitored at 310 nm, 2 mm path). A peak containing S(−) tofisopam is collected from the third recycle, dried and stored for use in biological assays.

The final preparation of (S)-tofisopam is assayed for enantiomeric purity and is found to be 87% pure (i.e., enantiomeric excess of 74%), as determined by analytical chromatography using Chiral Tech OD GH060 columns (Daicel) (hexane/IPA 90/10, 25° C. detection at 310 nm).

Example 2

Decrease of Serum Uric Acid Levels in Males

Male healthy volunteers received 50-400 mg enantiomerically-pure (S)-tofisopam by oral administration. Mean serum uric acid values fell by 23% to 30% within 4 hours after receiving single doses (Table 1). Uric acid levels decreased further up to the 24-hour timepoint, with no further decrease at 48 hours. Decreases were dose-related up to the 300 mg dose, with slightly lower decreases at 400 mg. Subjects receiving a single dose of placebo showed a slight increase in uric acid levels at 4 hours and small reductions at 24 and 48 hours.

TABLE 1

Change from Baseline in Uric Acid Levels Following Single Doses of Enantiomerically-pure (S)-tofisopam in Healthy Volunteers

| | Single Dose of (S)-tofisopam | | | | | |
|---|---|---|---|---|---|---|
| Time After Dose | 50 mg Mean CFB (n = 6) | 100 mg Mean CFB (n = 6) | 200 mg Mean CFB (n = 6) | 300 mg Mean CFB (n = 6) | 400 mg Mean CFB (n = 6) | Placebo Mean CFB (n = 12) |
| 4 hours | −23% | −25% | −29% | −30% | −27% | 1% |
| 24 hours | −25% | −28% | −36% | −48% | −48% | −3% |
| 48 hours | −24% | −29% | −37% | −49% | −45% | −9% |

Abbreviation: CFB, change from baseline

Example 3

Decrease of Serum Uric Acid Levels in Males and Females

In another study in healthy men and postmenopausal women, the trial period included a single-dose phase (Day 1) and a multiple-dose phase (Days 2-6). Decreased uric acid levels were noted in both men and women as early as 24 hours (the first post-dose assessment) after oral administration of a single dose of either 50 mg or 150 mg (Day 1) (S)-tofisopam. With multiple-dose oral administration (twice a day (BID) or three times a day (TID) on days 2-6), this decrease was more pronounced. As shown in Table 2, by the morning of Day 4, large (>50%) reductions from baseline were observed in male and female subjects treated with 50 mg TID or 150 mg BID enantiomerically-pure (S)-tofisopam, and these reductions were sustained through the end of the 7-day treatment period. By contrast, no notable or consistent changes in uric acid levels were seen in subjects given placebo. A post hoc analysis of clinical trial specimens indicates that enantiomerically-pure (S)-tofisopam 50 mg TID increases the fractional excretion of uric acid with no sign of renal injury, showing no measurable effect on other common parameters of renal function.

TABLE 2

Change from Baseline Serum Uric Acid Values During Treatment
with Enantiomerically-pure (S)-tofisopam or Placebo

| | 50 mg TID[a] (S)-tofisopam | | | | 150 mg BID[a] (S)-tofisopam | | | | Placebo[a] | | |
|---|---|---|---|---|---|---|---|---|---|---|---|
| | | Change from Baseline | | | | Change from Baseline | | | | Change from Baseline | |
| Population | N | Day 2 AM | Day 4 AM | Day 7 AM | N | Day 2 AM | Day 4 AM | Day 7 AM | N | Day 2 AM | Day 4 AM | Day 7 AM |
| Young men | 6 | −19% | −63% | −59% | 6[b] | −31% | −72% | −72% | 4 | 0% | −7% | −4% |
| Postmenopausal women | 18 | −27% | −58% | −65% | 17 | −48% | −76% | −71% | 12 | 0% | +5% | +5% |

Abbreviations: AM, morning; CFB, change from baseline; N, number of subjects; SD, standard deviation.
[a] All subjects received a single dose the morning of Day 1, with no further doses on Day 1.
[b] N = 5 on Days 4 and 7 for men receiving 150 mg BID.

The precise mechanism by which enantiomerically-pure (S)-tofisopam lowers uric acid is unknown. Without wishing to be bound by one theory, it seems that unlike allopurinol, enantiomerically-pure (S)-tofisopam does not inhibit xanthine oxidase. Available data indicate that the predominant mechanism of the scrum-urate lowering effect of enantiomerically-pure (S)-tofisopam is through uricosuric activity rather than inhibition of urate synthesis.

Comparative Example 4
Enantiomerically-Pure (R)-Tofisopam does not Decrease Serum Uric Acid Levels in Postmenopausal Women In a double-blind, randomized, placebo-controlled, single- and multiple-dose study in postmenopausal women with enantiomerically-pure (R)-tofisopam, patients were treated with placebo, 100 mg once a day (qd) of (R)-tofisopam, or 200 mg qd of (R)-tofisopam for the first day of the study, and then with placebo, 100 mg twice a day (bid) of (R)-tofisopam, or 200 mg bid of (R)-tofisopam for Days 2 to 7 of the study. The study demonstrated that (R)-tofisopam does not decrease serum uric acid levels. As shown in Table 3, serum uric acid levels remained constant up to 168 hours (7 days) after initiation of treatment with (R)-tofisopam.

TABLE 3

Mean Values and Change from Baseline Serum Uric Acid Values During
Treatment with Enantiomerically-pure (R)-tofisopam or Placebo

| Treatment | Protocol Scheme Time (h) | Unadjusted data | | | | | | Baseline adjusted data | | | | |
|---|---|---|---|---|---|---|---|---|---|---|---|---|
| | | N | Mean | SD | Median | Min | Max | N | Mean | SD | Median | Min | Max |
| Placebo | Screening | 12 | 0.23 | 0.04 | 0.23 | 0.17 | 0.29 | | | | | |
| | Admission | 12 | 0.20 | 0.04 | 0.20 | 0.14 | 0.27 | | | | | |
| | −1 | 12 | 0.19 | 0.03 | 0.19 | 0.14 | 0.23 | | | | | |
| | 6 | 12 | 0.20 | 0.03 | 0.21 | 0.15 | 0.24 | 12 | 0.01 | 0.01 | 0.01 | −0.01 | 0.03 |
| | 24 | 12 | 0.20 | 0.03 | 0.21 | 0.15 | 0.23 | 12 | 0.01 | 0.01 | 0 | −0.01 | 0.02 |
| | 72 | 12 | 0.20 | 0.03 | 0.20 | 0.15 | 0.24 | 12 | 0.01 | 0.02 | 0 | −0.01 | 0.05 |
| | 143 | 12 | 0.20 | 0.03 | 0.20 | 0.16 | 0.23 | 12 | 0.01 | 0.02 | 0 | −0.02 | 0.04 |
| | 168 | 12 | 0.21 | 0.03 | 0.22 | 0.15 | 0.28 | 12 | 0.02 | 0.03 | 0.02 | −0.03 | 0.06 |
| 100 mg bid | Screening | 16 | 0.22 | 0.06 | 0.22 | 0.11 | 0.36 | 16 | | | | | |
| | Admission | 16 | 0.21 | 0.05 | 0.22 | 0.10 | 0.28 | 16 | | | | | |
| | −1 | 16 | 0.19 | 0.05 | 0.20 | 0.07 | 0.26 | 16 | | | | | |
| | 6 | 16 | 0.19 | 0.04 | 0.19 | 0.08 | 0.26 | 16 | 0 | 0.01 | 0 | −0.02 | 0.01 |
| | 24 | 16 | 0.20 | 0.04 | 0.21 | 0.09 | 0.26 | 16 | 0.01 | 0.01 | 0.01 | −0.01 | 0.02 |
| | 72 | 16 | 0.20 | 0.04 | 0.21 | 0.09 | 0.25 | 16 | 0.01 | 0.02 | 0.01 | −0.02 | 0.03 |
| | 143 | 16 | 0.20 | 0.04 | 0.20 | 0.10 | 0.26 | 16 | 0.01 | 0.02 | 0.01 | −0.02 | 0.03 |
| | 168 | 16 | 0.23 | 0.04 | 0.23 | 0.11 | 0.28 | 16 | 0.03 | 0.02 | 0.03 | 0.01 | 0.06 |
| 200 mg bid | Screening | 18 | 0.24 | 0.05 | 0.26 | 0.12 | 0.32 | 18 | | | | | |
| | Admission | 18 | 0.22 | 0.04 | 0.23 | 0.14 | 0.29 | 18 | | | | | |
| | −1 | 18 | 0.22 | 0.03 | 0.21 | 0.15 | 0.27 | 18 | | | | | |
| | 6 | 18 | 0.21 | 0.03 | 0.21 | 0.14 | 0.27 | 18 | −0.01 | 0.01 | −0.01 | −0.03 | 0.01 |
| | 24 | 18 | 0.21 | 0.04 | 0.21 | 0.14 | 0.26 | 18 | −0.01 | 0.01 | −0.01 | −0.04 | 0.02 |
| | 72 | 18 | 0.22 | 0.04 | 0.22 | 0.15 | 0.29 | 18 | 0 | 0.02 | 0 | −0.03 | 0.03 |
| | 143 | 18 | 0.21 | 0.04 | 0.21 | 0.14 | 0.28 | 18 | −0.01 | 0.03 | 0 | −0.07 | 0.02 |
| | 168 | 18 | 0.22 | 0.04 | 0.23 | 0.16 | 0.31 | 18 | 0.01 | 0.02 | 0.01 | −0.04 | 0.05 |

SD: standard deviation D: day
* qd on D 1 and bid on D 2 to D 7

Comparative Example 5

Enantiomerically-Pure (R)-Tofisopam does not Decrease Serum Uric Acid Levels in Men and Women with Irritable Bowel Syndrome In a double-blind, randomized, placebo-controlled study of enantiomerically-pure (R)-tofisopam in male and female outpatients with irritable bowel syndrome, it was demonstrated that (R)-tofisopam does not decrease serum uric acid levels. The study lasted 3 months, and patients were treated with 200 mg of (R)-tofisopam twice a day (bid). As shown in Table 4, serum uric acid levels remained constant up to 3 months after initiation of treatment with enantiomerically-pure (R)-tofisopam.

TABLE 4

Mean Values and Change from Baseline Serum Uric Acid Values During Treatment with Enantiomerically-pure (R)-tofisopam or Placebo

| | | (R)-tofisopam (N = 66) | | Placebo (N = 74) | |
| --- | --- | --- | --- | --- | --- |
| Time | Statistic | Actual Value | Change from Baseline | Actual Value | Change from Baseline |
| Screening | N | 66 | | 74 | |
| | Mean | 5.42 | | 5.30 | |
| | Median | 5.10 | | 5.35 | |
| | SD | 1.442 | | 1.446 | |
| | Range | 2.8-9.5 | | 2.3-8.9 | |
| Baseline | N | 64 | | 72 | |
| | Mean | 5.30 | | 5.33 | |
| | Median | 5.20 | | 5.20 | |
| | SD | 1.499 | | 1.533 | |
| | Range | 2.0-11.0 | | 2.1-8.8 | |
| Day 7 | N | 63 | 63 | 70 | 70 |
| | Mean | 5.18 | −0.05 | 5.32 | 0.04 |
| | Median | 5.00 | 0.00 | 5.40 | 0.05 |
| | SD | 1.284 | 0.739 | 1.494 | 0.770 |
| | Range | 2.7-8.5 | −2.5-2.5 | 2.3-8.9 | −2.9-1.6 |
| Day 14 | N | 60 | 60 | 70 | 70 |
| | Mean | 5.22 | −0.01 | 5.29 | 0.04 |
| | Median | 5.05 | −0.10 | 5.40 | 0.15 |
| | SD | 1.494 | 0.721 | 1.426 | 0.743 |
| | Range | 2.3-8.9 | −2.1-1.8 | 2.5-8.8 | −1.7-2.1 |
| Day 28 | N | 58 | 58 | 64 | 64 |
| | Mean | 5.18 | −0.07 | 5.15 | −0.07 |
| | Median | 5.00 | −0.10 | 5.05 | −0.05 |
| | SD | 1.559 | 0.722 | 1.588 | 0.789 |
| | Range | 1.6-9.4 | −1.6-1.8 | 2.2-9.0 | −2.5-2.1 |
| Day 42 | N | 53 | 53 | 60 | 60 |
| | Mean | 5.46 | 0.12 | 5.27 | 0.02 |
| | Median | 5.70 | 0.20 | 5.30 | 0.10 |
| | SD | 1.484 | 0.766 | 1.559 | 0.849 |
| | Range | 2.6-10.2 | −1.8-1.4 | 2.4-9.3 | −2.7-1.5 |
| Day 56 | N | 51 | 51 | 58 | 58 |
| | Mean | 5.40 | 0.02 | 5.33 | 0.05 |
| | Median | 5.20 | 0.00 | 5.20 | 0.15 |
| | SD | 1.574 | 0.588 | 1.608 | 0.968 |
| | Range | 2.6-9.6 | −1.4-1.1 | 2.5-10.2 | −2.6-3.6 |
| Day 84 | N | 47 | 47 | 54 | 54 |
| | Mean | 5.37 | 0.03 | 5.30 | −0.01 |
| | Median | 5.30 | 0.10 | 5.30 | 0.00 |
| | SD | 1.380 | 0.709 | 1.518 | 0.848 |
| | Range | 3.0-8.9 | −2.1-1.6 | 2.5-8.6 | −2.2-1.8 |
| 3 months Endpoint | N | 64 | 64 | 71 | 71 |
| | Mean | 5.20 | −0.06 | 5.24 | −0.03 |
| | Median | 5.10 | 0.00 | 5.30 | 0.00 |
| | SD | 1.418 | 0.681 | 1.511 | 0.807 |
| | Range | 1.6-8.9 | −2.1-1.6 | 2.4-8.6 | −2.2-1.8 |

SD: standard deviation

Comparative Example 6

Enantiomerically-Pure (R)-Tofisopam does not Decrease Serum Uric Acid Levels in Women with Irritable Bowel Syndrome In a double-blind, randomized, placebo-controlled study of enantiomerically-pure (R)-tofisopam in female outpatients with irritable bowel syndrome, it was demonstrated that (R)-tofisopam does not decrease serum uric acid levels. The study lasted 3 months, and patients were treated with 100 mg, 200 mg or 300 mg of enantiomerically-pure (R)-tofisopam twice a day. As shown in Table 5, serum uric acid levels remained constant up to 3 months after initiation of treatment with enantiomerically-pure (R)-tofisopam.

TABLE 5

Mean Values and Change from Baseline Serum Uric Acid Values During Treatment with up to 300 mg BID Enantiomerically-pure (R)-tofisopam or Placebo

| | | Placebo (N = 79) | | (R)-tofisopam 100 mg BID (N = 82) | |
| --- | --- | --- | --- | --- | --- |
| Time | Statistic | Actual Value | Change from Baseline | Actual Value | Change from Baseline |
| Week 12 | N | 57 | 57 | 61 | 61 |
| | Mean | 4.63 | 0.06 | 4.91 | 0.23 |
| | Median | 4.60 | 0.10 | 4.80 | 0.20 |
| | SD | 0.905 | 0.628 | 1.338 | 0.738 |
| | Min | 2.6 | −1.3 | 1.9 | −1.2 |
| | Max | 6.4 | 1.5 | 9.4 | 3.0 |
| 3 months Endpoint | N | 70 | 70 | 72 | 72 |
| | Mean | 4.70 | 0.10 | 4.94 | 0.22 |
| | Median | 4.60 | 0.10 | 4.90 | 0.20 |
| | SD | 1.034 | 0.608 | 1.317 | 0.698 |
| | Min | 2.6 | −1.3 | 1.9 | −1.2 |
| | Max | 8.3 | 1.5 | 9.4 | 3.0 |

| | | (R)-tofisopam 200 mg BID (N = 79) | | (R)-tofisopam 300 mg BID (N = 79) | |
| --- | --- | --- | --- | --- | --- |
| Time | Statistic | Actual Value | Change from Baseline | Actual Value | Change from Baseline |
| Week 12 | N | 62 | 62 | 60 | 60 |
| | Mean | 4.82 | −0.20 | 5.02 | −0.06 |
| | Median | 4.60 | −0.20 | 4.95 | −0.05 |
| | SD | 1.043 | 0.662 | 1.192 | 0.832 |
| | Min | 2.4 | −2.1 | 2.6 | −2.2 |
| | Max | 7.4 | 1.5 | 7.9 | 1.6 |
| 3 months Endpoint | N | 69 | 69 | 65 | 65 |
| | Mean | 4.82 | −0.19 | 5.04 | −0.05 |
| | Median | 4.60 | −0.20 | 5.00 | 0.00 |
| | SD | 1.023 | 0.656 | 1.162 | 0.821 |
| | Min | 2.4 | −2.1 | 2.6 | −2.2 |
| | Max | 7.4 | 1.5 | 7.9 | 1.6 |

SD: standard deviation

Example 7

Enantiomerically-Pure (S)-Tofisopam Decreases Serum Uric Acid Levels in Men and Postmenopausal Women with Hyperuricemia and Gout In an open-label, randomized, inpatient study of enantiomerically-pure (S)-tofisopam in male and female patients with hyperuricemia and gout, it was demonstrated that (S)-tofisopam decreases serum uric acid levels. The study lasted 7 days, and patients were treated with placebo or 50 mg of enantiomerically-pure (S)-tofisopam once a day (qd) on Day 1 and Day 7 of the study, and with placebo or 50 mg of enantiomerically-pure (S)-tofisopam three times a day (tid) for Days 2 to 6 of the study. As shown in Table 6, serum uric acid levels decreased after initiation of treatment with of enantiomerically-pure (S)-tofisopam. Once treatment was stopped after 7 days, serum uric acid levels began to increase again. In Table 6, days indicated with a minus sign (e.g. D-1) indicate the time point corresponding to that number of days before treatment was initiated. For example, D-14 is the time point fourteen days before treatment was initiated.

with hyperuricemia and gout, it was demonstrated that (S)-tofisopam does not modify serum creatinine levels. The study lasted 7 days, and patients were treated with placebo or 50 mg of enantiomerically-pure (S)-tofisopam once a day (qd) on Day 1 and Day 7 of the study, and with placebo or 50 mg of enantiomerically-pure (S)-tofisopam three times a day (tid) for Days 2 to 6 of the study. As shown in Table 7, serum creatinine levels did not substantially change after initiation

TABLE 6

Percent Change in Serum Uric Acid Values During Treatment with 50 mg TID Enantiomerically-pure (S)-tofisopam

| | | | | | | Day 1 to Day 2 | | | | | | | | | | |
|---|---|---|---|---|---|---|---|---|---|---|---|---|---|---|---|---|
| | D -21 | ** | Day -2 to Day -1 | | | | | Day 1 | | * | | | Day 6 to Day 7 | | | |
| P# | to D -14 Screen | Day -3 % | Day -2 % | Day -1 % | D -2 + D -1 % | Day 1 % 0 h | Day 1 % 6 h | Day 2 % | 0 h + Day 2 % | Day 3 % | Day 4 % | Day 5 % | Day 6 % | Day 7 % | Day 6 + Day 7 % | Day 8 % | Day 15 % |
| 1 | 8.5 | 0.0 | -6.5 | -12.9 | -9.7 | 0.0 | -1.2 | -15.3 | -7.6 | -31.8 | -35.5 | -41.2 | -43.5 | -51.8 | -47.6 | -36.5 | 16.5 |
| 2 | 8.3 | 0.0 | -4.7 | -16.3 | -10.5 | 0.0 | -12.0 | -21.3 | -10.7 | -32.0 | -38.7 | -48.0 | -40.0 | -48.0 | -44.0 | -36.0 | 36.0 |
| 3 | 8.0 | 0.0 | 0.0 | -11.1 | -5.6 | 0.0 | 4.1 | -19.2 | -9.6 | -43.8 | -54.8 | -52.1 | -53.4 | -58.9 | -56.2 | -46.6 | 17.8 |
| 4 | 8.0 | 0.0 | -2.7 | -5.5 | -4.1 | 0.0 | -4.3 | -8.6 | -4.3 | -14.3 | -27.1 | -40.0 | -31.4 | -41.4 | -36.4 | -32.9 | 25.7 |
| 5 | 8.2 | 0.0 | 2.5 | 0.0 | 1.3 | 0.0 | -8.0 | -14.7 | -7.3 | -30.7 | -42.7 | -36.0 | -64.0 | -48.0 | -56.0 | -36.0 | -13.3 |
| 6 | 10.2 | 0.0 | 36.1 | 34.7 | 35.4 | 0.0 | -12.5 | -17.7 | -8.9 | -36.5 | -43.8 | -45.8 | -45.8 | -47.9 | -46.9 | -41.7 | 1.0 |
| 7 | 9.1 | 0.0 | 17.1 | 13.2 | 15.1 | 0.0 | -8.1 | -16.2 | -8.1 | -18.9 | -37.8 | -33.8 | -31.1 | -31.1 | -31.1 | -24.3 | 39.2 |
| 8 | 8.7 | 0.0 | 3.2 | -6.5 | -1.6 | 0.0 | -13.9 | -24.1 | -12.0 | -45.6 | -54.4 | -50.6 | -50.6 | -55.7 | -53.2 | -45.6 | 30.4 |
| 9 | 9.3 | 0.0 | -3.0 | -6.0 | -4.5 | 0.0 | -8.2 | -5.2 | -2.6 | -12.4 | -59.8 | -25.8 | -28.9 | -40.2 | -34.5 | -30.9 | 10.3 |
| 10 | 8.0 | 0.0 | 0.0 | -8.4 | -4.2 | 0.0 | -5.6 | -7.0 | -3.5 | -16.9 | -35.2 | -39.4 | -39.4 | -42.3 | -40.8 | -26.8 | 26.8 |
| 11 | 11.2 | 0.0 | 11.5 | 3.8 | 7.7 | 0.0 | -6.0 | 0.0 | 0.0 | -9.6 | -30.1 | -39.8 | -45.8 | -53.0 | -49.4 | -33.7 | 18.1 |
| 12 | 9.7 | 0.0 | -4.3 | -20.4 | -12.4 | 0.0 | -13.3 | -9.3 | -4.7 | -29.3 | -37.3 | -38.7 | -45.3 | -52.0 | -48.7 | -36.0 | 18.7 |
| 13 | 9.0 | 0.0 | 2.2 | -6.5 | -2.2 | 0.0 | -14.6 | -19.5 | -9.8 | -40.2 | -57.3 | -58.5 | -58.5 | -64.6 | -61.6 | -51.2 | 24.4 |
| M | 5.8 | 0.0 | 4.9 | -1.4 | 1.8 | 0.0 | -6.9 | -13.6 | -6.8 | -26.6 | -41.8 | -41.1 | -43.1 | -47.1 | -45.1 | -35.5 | 18.9 |
| sd | 444.2% | 0.0 | 12.5 | 14.5 | 13.4 | 0.0 | 5.2 | 7.4 | 3.7 | 12.7 | 10.6 | 7.8 | 10.6 | 8.0 | 8.6 | 7.0 | 15.4 |

D: day sd: standard deviation M: mean P#: patient's number
* Indomethacin initiated for pain in subjects 6 and 7 on study D 3 and stopped on study D 6 and D 7, respectively.
** Subject 9 received indomethacin and/or acetaminophen from D -3 through D 3.

Example 8

Enantiomerically-pure (S)-tofisopam Does Not Modify Serum Creatinine Levels in Men and Postmenopausal Women with Hyperuricemia and Gout In an open-label, randomized, inpatient study of enantiomerically-pure (S)-tofisopam in male and female patients of treatment with of enantiomerically-pure (S)-tofisopam. Once treatment was stopped after 7 days, serum creatinine levels did not substantially change. In Table 7, days indicated with a minus sign (e.g. D-1) indicate the time point corresponding to that number of days before treatment was initiated. For example, D-14 is the time point fourteen days before treatment was initiated.

TABLE 7

Percent Change in Serum Creatinine Values During Treatment with 50 mg TID Enantiomerically-pure (S)-tofisopam

| | | | | | | Day 1 to Day 2 | | | | | | | | | | |
|---|---|---|---|---|---|---|---|---|---|---|---|---|---|---|---|---|
| | D -21 | ** | Day -2 to Day -1 | | | | | Day 1 | | * | | | Day 6 to Day 7 | | | |
| P# | to D -14 Screen | Day -3 % | Day -2 % | Day -1 % | D -2 + D -1 % | Day 1 % 0 h | Day 1 % 6 h | Day 2 % | 0 h + Day 2 % | Day 3 % | Day 4 % | Day 5 % | Day 6 % | Day 7 % | Day 6 + Day 7 % | Day 8 % | Day 15 % |
| 1 | 0.97 | 0.0 | -3.0 | -7.1 | -5.1 | 0.0 | 2.2 | 9.8 | 4.9 | 8.7 | 4.3 | 8.7 | 25.0 | 7.6 | 16.3 | 4.3 | 5.4 |
| 2 | 0.91 | 0.0 | -9.3 | -13.4 | -11.3 | 0.0 | 10.1 | 8.9 | 4.4 | 7.6 | 3.8 | -5.1 | 17.7 | 12.7 | 15.2 | 10.1 | 27.8 |
| 3 | 1.27 | 0.0 | -0.8 | -12.2 | -6.5 | 0.0 | 0.9 | 1.9 | 0.9 | 3.7 | -5.6 | -3.7 | 7.4 | -2.8 | 2.3 | -7.4 | 9.3 |
| 4 | 1.10 | 0.0 | -17.6 | -10.1 | -13.9 | 0.0 | 2.9 | 1.0 | 0.5 | 13.6 | 4.9 | 8.7 | 2.9 | -1.9 | 0.5 | -8.7 | 19.4 |
| 5 | 1.07 | 0.0 | -8.1 | -6.3 | -7.2 | 0.0 | 0.0 | -2.0 | -1.0 | 2.0 | -2.0 | 9.8 | 4.9 | -2.9 | 1.0 | -6.9 | 4.9 |
| 6 | 1.20 | 0.0 | 3.5 | -12.4 | -4.4 | 0.0 | 1.8 | 4.5 | 2.3 | 16.2 | 21.6 | 23.4 | 9.9 | 10.8 | 10.4 | 0.9 | 17.1 |
| 7 | 1.22 | 0.0 | -5.3 | 0.0 | -2.6 | 0.0 | 5.7 | 0.9 | 0.5 | 10.4 | -2.8 | 0.9 | 0.0 | 11.3 | 5.7 | -2.8 | 23.6 |

TABLE 7-continued

Percent Change in Serum Creatinine Values During Treatment with 50 mg TID Enantiomerically-pure (S)-tofisopam

| P# | D −21 to D −14 Screen | ** Day −3 % | Day −2 to Day −1 | | | Day 1 to Day 2 | | | Day 1 | | * | | | Day 6 to Day 7 | | | Day 8 % | Day 15 % |
|---|---|---|---|---|---|---|---|---|---|---|---|---|---|---|---|---|---|---|
| | | | Day −2 % | Day −1 % | D −2 + D −1 % | Day 1 % 0 h | Day 1 % 6 h | Day 2 % | 0 h + Day 2 % | Day 3 % | Day 4 % | Day 5 % | Day 6 % | Day 7 % | Day 6 + Day 7 % | | |
| 8  | 0.73  | 0.0 | −1.4 | −6.9  | −4.2 | 0.0 | 4.8   | 1.6   | 0.8  | 4.8  | 3.2   | 14.3 | 6.3  | 7.9   | 7.1  | 12.7 | 25.4  |
| 9  | 0.87  | 0.0 | −9.4 | −9.4  | −9.4 | 0.0 | 10.3  | −2.6  | −1.3 | 17.9 | 14.1  | 7.7  | 7.7  | 2.6   | 5.1  | 12.8 | −2.6  |
| 10 | 1.01  | 0.0 | −1.1 | −6.5  | −3.8 | 0.0 | 0.0   | 13.3  | 6.7  | 24.0 | 18.7  | 24.0 | 18.7 | 5.3   | 12.0 | 24.0 | 46.7  |
| 11 | 1.25  | 0.0 | −6.3 | −0.9  | −3.6 | 0.0 | 1.0   | 5.9   | 3.0  | 14.9 | 18.8  | 5.9  | 5.9  | 3.0   | 4.5  | 6.9  | 16.8  |
| 12 | 1.02  | 0.0 | 18.2 | 10.2  | 14.2 | 0.0 | −2.9  | −5.8  | −2.9 | −1.9 | −3.8  | −1.0 | −8.7 | −10.6 | −9.6 | −1.9 | −12.5 |
| 13 | 1.08  | 0.0 | 6.9  | −4.0  | 1.5  | 0.0 | −4.0  | −10.0 | −5.0 | 9.0  | 4.0   | 0.0  | 6.0  | 5.0   | 5.5  | 5.0  | −4.0  |
| M  | 1.05  | 0.0 | −2.6 | −6.1  | −4.3 | 0.0 | 2.5   | 2.1   | 1.1  | 10.1 | 6.1   | 7.2  | 8.0  | 3.7   | 5.8  | 3.8  | 13.6  |
| sd | 16.0% | 0.0 | 8.8  | 6.4   | 6.8  | 0.0 | 4.3   | 6.5   | 3.2  | 7.2  | 9.3   | 9.3  | 8.6  | 6.8   | 6.9  | 9.6  | 15.8  | sd: standard deviation M: mean P#: patient number
* Indomethacin initiated for pain in subjects 6 and 7 on study D 3 and stopped on study D 6 and D 7, respectively.
** Subject 9 received indomethacin and/or acetaminophen from D −3 through D 3.

Example 9

Enantiomerically-Pure (S)-Tofisopam Increases Urinary Uric Acid Excretion Levels in the Urine of Men and Postmenopausal Women with Hyperuricemia and Gout In an open-label, randomized, inpatient study of enantiomerically-pure (S)-tofisopam in male and female patients with hyperuricemia and gout, it was demonstrated that (S)-tofisopam decreases serum uric acid levels by increasing the excretion of uric acid in the urine. The study lasted 7 days, and patients were treated with placebo or 50 mg of enantiomerically-pure (S)-tofisopam once a day (qd) on Day 1 and Day 7 of the study, and with placebo or 50 mg of enantiomerically-pure (S)-tofisopam three times a day (tid) for Days 2 to 6 of the study. As shown in Table 8, uric acid excretion levels increased after initiation of treatment with enantiomerically-pure (S)-tofisopam. In Table 8, days indicated with a minus sign (e.g. D-1) indicate the time point corresponding to that number of days before treatment was initiated. For example, D-14 is the time point fourteen days before treatment was initiated.

TABLE 8

Percent Change in 24 h Urinary Creatinine and Uric Acid Excretions and Fractional Excretion of Urate after Treatment with Enantiomerically-pure (S)-tofisopam

| | Day −2 to Day −1 | | | | | | | 24 hour urinary changes [D 1 to D 2] from [D −2 to D −1] | | | | | | |
|---|---|---|---|---|---|---|---|---|---|---|---|---|---|---|
| P # | 24 h Vol (mL) | CLc (ml/min) | Uc (mg/24 h) | Uc (mg/dL) | Uu (mg/24 h) | Uu (mg/dL) | FEu (%) | 24 h Vol (mL) | CLc (ml/min) | Uc (mg/24 h) | Uc (mg/dL) | Uu (mg/24 h) | Uu (mg/dL) | FEu (%) |
| 1  | 2900 | 134.0 | 1780.6 | 61.4  | 727.9 | 25.1 | 4.6 | −13.8 | 35.1  | 47.6  | 71.2  | 14.4  | 32.7  | −14.9 |
| 2  | 3000 | 122.0 | 1470.0 | 49.0  | 627.0 | 20.9 | 4.8 | 23.3  | 2.5   | 5.5   | −14.5 | 6.5   | −13.4 | 11.7  |
| 3  | 2300 | 119.0 | 1846.9 | 80.3  | 696.9 | 30.3 | 5.7 | −32.6 | −24.4 | −22.9 | 14.4  | −29.9 | 4.0   | −0.2  |
| 4  | 1250 | 183.0 | 2824.9 | 217.3 | 728.0 | 56.0 | 3.8 | 0.8   | −14.2 | −16.8 | −14.1 | 12.0  | 15.5  | 41.9  |
| 5  | 1100 | 136.0 | 2036.1 | 185.1 | 757.9 | 68.9 | 4.7 | 100.0 | 16.2  | 11.5  | −44.2 | −55.4 | −77.6 | −54.2 |
| 6  | 2750 | 134.0 | 1905.8 | 69.3  | 462.0 | 16.8 | 2.7 | −3.3  | −22.4 | −8.7  | −5.6  | 85.4  | 91.7  | 137.8 |
| 7  | 4200 | 151.0 | 2472.8 | 56.2  | 831.6 | 18.9 | 4.3 | −36.7 | 0.7   | −5.2  | 56.8  | 25.1  | 106.9 | 62.9  |
| 8  | 2150 | 146   | 1404   | 65    | 555   | 26   | 3.0 | 16.3  | −4.1  | −8.1  | −21.0 | 99.2  | 71.3  | 162.7 |
| 9  | 2050 | 146   | 1827   | 89    | 517   | 25   | 2.6 | 26.8  | −2.7  | −15.0 | −33.0 | 43.4  | 13.1  | 51.0  |
| 10 | 1900 | 139   | 1742   | 92    | 536   | 28   | 3.5 |       |       |       |       |       |       |       |
| 11 | 2075 | 153   | 2417   | 117   | 726   | 35   | 3.8 | −8.4  | −1.3  | −3.5  | 5.4   | −30.9 | −24.6 | −29.6 |
| 12 | 1825 | 136   | 1902   | 104   | 703   | 39   | 4.6 | 38.1  | −11.8 | −11.0 | −35.5 | −7.1  | −32.7 | 19.5  |
| 13 | 2990 | 125   | 1740   | 58    | 661   | 22   | 4.3 | −17.4 | 11.2  | 3.8   | 25.6  | 27.8  | 54.8  | 40.4  |
| M  | 2345.4 | 140.3 | 1951.5 | 95.7 | 656.0 | 31.7 | 4.0 | 7.8   | −1.3  | −1.9  | 0.5   | 15.9  | 20.1  | 35.8  |
| sd | 825.4  | 16.6  | 402.0  | 51.3 | 109.2 | 15.2 | 0.0 | 0.4   | 0.2   | 0.2   | 0.4   | 0.5   | 0.5   | 0.6   |

TABLE 8-continued

Percent Change in 24 h Urinary Creatinine and Uric Acid Excretions and Fractional Excretion of Urate after Treatment with Enantiomerically-pure (S)-tofisopam

| | | 24 hour urinary changes [D 6 to D 7] from [D 1 to D 2] | | | | | |
|---|---|---|---|---|---|---|---|
| P # | 24 h Vol (mL) | CLc (ml/min) | Uc (mg/24 h) | Uc (mg/dL) | Uu (mg/24 h) | Uu (mg/dL) | FEu (%) |
| 1 | 24.0 | −12.7 | −14.5 | −31.0 | 4.6 | −15.6 | 139.3 |
| 2 | 18.9 | 15.2 | 19.2 | 0.2 | 21.3 | 1.7 | 78.5 |
| 3 | 74.2 | 21.1 | 15.4 | −33.7 | 43.8 | −17.5 | 160.4 |
| 4 | 40.9 | 14.0 | 10.8 | −21.3 | 18.3 | −15.9 | 60.9 |
| 5 | 27.3 | 8.9 | 7.9 | −15.2 | 1.0 | −20.8 | 100.7 |
| 6 | 56.0 | 0.0 | 5.9 | −32.1 | −7.0 | −40.4 | 62.6 |
| 7 | 71.1 | −3.9 | 5.6 | −38.3 | −11.6 | −48.3 | 17.3 |
| 8 | 60.0 | 14.3 | 21.6 | −24.0 | −18.9 | −49.3 | 33.2 |
| 9 | 19.2 | 0.7 | 5.8 | −11.2 | 7.9 | −9.5 | 61.6 |
| 10 | | | | | | | |
| 11 | | | | | | | |
| 12 | 1.2 | 0.0 | −4.8 | −6.0 | −13.3 | −14.3 | 57.5 |
| 13 | 27.5 | −23.7 | −10.8 | −30.1 | −22.8 | −39.5 | 125.9 |
| M | | 3.1 | 5.6 | −22.1 | 2.1 | −24.5 | 81.6 |
| sd | | 0.1 | 0.1 | 0.1 | 0.2 | 0.2 | 0.4 | sd: standard deviation M: mean
CLc (ml/min): clearance creatinine, expressed as a volume per minute of creatinine that is cleared from the blood serum or plasma and excreted (ml/min) into the urine.
Uc (mg/24 h): the amount (mg) of creatinine excreted into the urine or removed from the blood serum or plasma over a period of 24 hours.
Uc (mg/dL): the concentration of creatinine in a volume of urine collected over a 24 hour period of time.
Uu (mg/24 h): the amount (mg) of uric acid excreted into the urine or removed from the blood serum or plasma over a period of 24 hours.
Uu (mg/dL): the concentration of uric acid in a volume of urine collected over a 24 hour period of time.
FEu (%): fractional excretion uric acid; it is expressed as a percentage of uric acid excreted in relation to the amount of creatinine excreted.
Note:
Incomplete collection for subject 10 (some data not included)
Lab collection error for subjects 10 and 11 (some data not included)

All references cited herein are incorporated by reference. The present invention may be embodied in other specific forms without departing from the spirit or essential attributes thereof and, accordingly, reference should be made to the appended claims, rather than to the foregoing specification, as indication of the scope of the invention.

What is claimed is:

1. A method of lowering serum uric acid levels in a mammal in need of such treatment, comprising administering to the mammal an effective amount of enantiomerically-pure (S)-tofisopam, or a pharmaceutically acceptable salt thereof.

2. The method according to claim 1, wherein said enantiomerically-pure (S)-tofisopam comprises 85% by weight or greater of (S)-tofisopam.

3. The method according to claim 1, wherein said enantiomerically-pure (S)-tofisopam comprises 90% by weight or greater of (S)-tofisopam.

4. The method according to claim 1, wherein said enantiomerically-pure (S)-tofisopam comprises 95% by weight or greater of (S)-tofisopam.

5. The method according to claim 1, wherein said enantiomerically-pure (S)-tofisopam comprises 99% by weight or greater of (S)-tofisopam.

6. The method according to claim 1, wherein said enantiomerically-pure (S)-tofisopam is administered with a second drug.

7. The method according to claim 1, wherein said mammal is afflicted with a disorder associated with elevated uric acid levels.

8. The method according to claim 7, wherein said disorder is selected from the group consisting of gout, urinary calculus, hyperuricemic nephropathy, Lesch-Nyhan syndrome, disorders of the hemocytopoietic organs, renal disorders, hypertension and disorders resulting from the administration of a medicament.

9. The method according to claim 8, wherein said disorder is gout.

10. The method according to claim 8, wherein said disorder is Lesch-Nyhan syndrome.

11. The method according to any one of claims 1-10, wherein said enantiomerically-pure (S)-tofisopam, or a pharmaceutically acceptable salt thereof, is administered at a daily dosage of 10 to 1500 mg/day.

12. The method according to claim 11, wherein said enantiomerically-pure (S)-tofisopam, or a pharmaceutically acceptable salt thereof, is administered at a daily dosage of 25 to 500 mg/day.

13. The method according to claim 11, wherein said enantiomerically-pure (S)-tofisopam, or a pharmaceutically acceptable salt thereof, is administered at a daily dosage of 50 to 400 mg/day.

14. The method according to claim 11, wherein said daily dosage of enantiomerically-pure (S)-tofisopam, or a pharmaceutically acceptable salt thereof, is administered as a single daily dose.

15. The method according to claim 11, wherein said daily dosage of enantiomerically-pure (S)-tofisopam, or a pharmaceutically acceptable salt thereof, is split into two, three or more doses per day.

16. The method according to claim 1, wherein said enantiomerically-pure (S)-tofisopam, or a pharmaceutically acceptable salt thereof, is administered orally.

17. The method according to claim 1, wherein said enantiomerically-pure (S)-tofisopam, or a pharmaceutically acceptable salt thereof, is administered at a dosage of 50 mg, three times a day.

18. The method according to claim 14, wherein said enantiomerically-pure (S)-tofisopam, or a pharmaceutically acceptable salt thereof, is administered as a single daily dose of 50 mg, 100 mg, 200 mg, 300 mg or 400 mg.

19. The method according to claim 1, wherein said uric acid is excreted.

* * * * *